(12) United States Patent
Sitther et al.

(10) Patent No.: US 12,024,704 B2
(45) Date of Patent: Jul. 2, 2024

(54) COMPOSITION AND METHOD FOR ENHANCING PHOTOSYNTHETIC EFFICIENCY, GROWTH AND/OR LIPID PRODUCTION OF MICROORGANISMS

(71) Applicant: Morgan State University, Baltimore, MD (US)

(72) Inventors: Viji Sitther, Pikesville, MD (US); Somayeh Fathabad, Parkville, MD (US)

(73) Assignee: Morgan State University, Baltimore, MD (US)

( * ) Notice: Subject to any disclaimer, the term of this patent is extended or adjusted under 35 U.S.C. 154(b) by 1029 days.

(21) Appl. No.: 16/712,125

(22) Filed: Dec. 12, 2019

(65) Prior Publication Data
US 2020/0131469 A1    Apr. 30, 2020

Related U.S. Application Data

(63) Continuation-in-part of application No. 15/678,643, filed on Aug. 16, 2017, now Pat. No. 11,162,067.

(60) Provisional application No. 62/778,617, filed on Dec. 12, 2018, provisional application No. 62/375,498, filed on Aug. 16, 2016.

(51) Int. Cl.
C12N 1/38    (2006.01)
C10L 1/02    (2006.01)
C12N 1/20    (2006.01)
C12P 7/649   (2022.01)

(52) U.S. Cl.
CPC .................. *C12N 1/38* (2013.01); *C10L 1/02* (2013.01); *C12N 1/20* (2013.01); *C12P 7/649* (2013.01); *C10L 2200/0476* (2013.01); *C10L 2290/26* (2013.01)

(58) Field of Classification Search
None
See application file for complete search history.

(56) References Cited

PUBLICATIONS

Pádrová et al., J. Appl. Phycol. 27: 1443-1451 (2015).*
Pattanaik et al., Microbiology 160: 992-1005 (2014).*

* cited by examiner

*Primary Examiner* — Erin M. Bowers
(74) *Attorney, Agent, or Firm* — Whiteford, Taylor & Preston, LLP; Peter J. Davis (57) ABSTRACT

Compositions including metal nano- and/or micro-particles in solution with photosynthetic bioproduct producing microorganisms. These light harvesting complexes increase growth rates and photosynthetic efficiency of the constituent microorganisms, reducing the light required for a specific production level, or increases production for a specific light level. Compositions including zero-valent iron nanoparticles (nZVIs) in solution with photosynthetic bioproduct producing microorganisms. The nZVIs cause increased growth, lipid production and fatty acid production.

5 Claims, 9 Drawing Sheets

COMPOSITION AND METHOD FOR ENHANCING PHOTOSYNTHETIC EFFICIENCY, GROWTH AND/OR LIPID PRODUCTION OF MICROORGANISMS

FIELD OF THE INVENTION

The present invention relates to compositions and methods for increasing the photosynthetic capacity, growth and/or lipid production of microorganisms.

DESCRIPTION OF THE BACKGROUND

The need and the market for microorganism propagation technology has expanded dramatically in the last decades with more and more "bioproducts" being produced experimentally and even commercially using specially engineered microorganisms. One important class of bioproducts is lipids. Lipids are naturally occurring molecules that include fats, waxes, sterols, fat-soluble vitamins (such as vitamins A, D, E, and K), monoglycerides, diglycerides, triglycerides, phospholipids, and others. Lipids are typically contained in photosynthetic bacteria and algae in the form of membrane components, storage products, and metabolites. Certain algal strains, particularly microalgae such as diatoms, certain chlorophyte species, and bacteria such as cyanobacteria, contain proportionally high levels of lipids. Algal sources for the algae oils can contain varying amounts, e.g., from 2 wt % to 40 wt % of lipids, based on total weight of the biomass itself.

Other bioproducts include biopolymers, nutraceuticals (e.g., vitamins) and pharmaceuticals; such as antimicrobials, antivirals, antifungals, neuroprotectives.

Another bioproduct is "biofuel," which includes fuel derived from biomass conversion. This renewable source of energy significantly contributes to energy security and alleviates the harmful effects of particulates, carbon monoxide and hydrocarbons in diesel-powered vehicles. With the negative impact of fossil fuel on the environment, it is more important than ever to find alternative sources of energy. Biofuel derived from cyanobacteria and algae has replaced around 1 billion gallons of petroleum diesel. The U.S. Department of Energy estimates that oil yields from cyanobacteria/algae range from 1,000-6,500 gallons/acre/year. Calculation and analysis of oil from lipids indicates a theoretical yield of 38,000 gallons/acre/year and a current practical yield of 4,350-5,700 gallons/acre/year from cyanobacteria/algae. These organisms convert light energy into chemical energy through photosynthesis. Since cyanobacteria provide very high levels of net energy, converting biomass into fuel is much less energy-intensive than other methods of conversion.

A recent analysis showed that current water and land resources in the U.S. could support the production of as much as 23.5 billion gallons/year (BGY) of algae-based fuel. The study also projected the number could be increased by 78.2 BGY (or 2.5 billion barrels/year) from biofuel production in saline waters. The U.S. Navy alone uses 36.5 million barrels of oil per year. It has mandated that 50% of its energy needs will be from domestic renewable fuel by 2020 as part of its national security strategy and it is investing heavily in the biofuel industry. The biofuel industry is expanding and is expected to double over the next 10 years into a $185 billion industry.

*Fremyella diplosiphon* has great potential as a production-scale biofuel agent. With a fast regeneration time and capability to grow in low light intensity as low as 15 µmol quanta $m^{-2}$ $s^{-1}$ and an optimal temperature of 28° C., it used as a model organism used to study photosynthesis. A light-dependent acclimation process known as complementary chromatic adaptation (CCA), enables the organism to absorb light and grow in a range of environmental conditions. CCA allows this species to live at various depths of the ocean, despite varying intensities of light. While several aspects of its growth in various wavelengths of light have been studied, there has been no attempt to enhance its photosynthetic potential, growth or lipid production using nanotechnology.

Nanoscale zero-valent iron nanoparticles (nZVIs) have received considerable attention for the reduction of organic and inorganic contaminants in the bioremediation of polluted waters, soils, and sediments, but there have been no reports on nZVI-mediated effect on total lipid yield and fatty acid (FA) composition.

SUMMARY OF THE INVENTION

The present inventions arise in part from the discovery by the inventors that nano- and micro-particles, when complexed to bioproduct-producing and biomass/biofuel photosynthetic microorganisms, can increase both the growth rate and the photosynthetic efficiency of the microorganism, as compared to non-complexed microorganisms. Accordingly, the artificial light harvesting complexes of the invention reduces the amount of artificial light (and associated costs) required for a certain bioreactor growth rate and/or increase the production capacity of a bioreactor without increasing costs.

The present inventions arise in further part from the discovery by the inventors that bioproduct-producing and biomass/biofuel photosynthetic microorganisms show significant increases in growth, total lipid content, and fatty acid composition when exposed to iron nanoparticles.

Accordingly, there is presented according to the invention a composition including a nano- and/or micro-particle complexed to a photosynthetic organism.

According to various embodiments of the invention, the particles of the complex may be metal particles, such as gold, silver, copper, and silicon, and microorganisms of the complex may be bacteria, algae, chlorophyte, protists, and fungi.

According to further embodiments of the invention, the photosynthetic bacteria may be selected from the group consisting of *F. diplosiphon*, *Nostoc* sp., *Tolypothrix* sp., *Calothrix* sp., *Synechococcus elongatus*, *Synechocystis* sp. PCC6803, *Arthrospira* sp., *Aphanothece* sp., and *Anabaena* sp.

According to a preferred embodiment of the invention, the microorganism may be *F. diplosiphon*.

According to a further preferred embodiment of the invention, the microorganism may be a strain of *F. diplosiphon* that has increased halotolerance relative to wild type strains.

According to a further preferred embodiment of the invention, the particle may be a gold nano-particle (also referred to as "GNP" and "AuNP").

According to still further embodiments of the invention, the photosynthetic algae may be selected from the group consisting of diatoms, *Chlorella* sp., *Nannochloris* sp., and *Dunaliella tertiolecta*.

According to still further embodiments of the invention, the microorganism may be suitable for use as a biofuel.

According to other embodiments of the invention, the microorganism may be a bioproduct producing microorganism. According to various sub-embodiments, the microorganism may produce lipids selected from the group consisting of fats, waxes, sterols, fat-soluble vitamins (such as vitamins A, D, E, and K), monoglycerides, diglycerides, triglycerides, and phospholipids.

According to further embodiments of the invention, the microorganism may produce bioproducts selected from the group consisting of biopolymers, nutraceuticals and pharmaceuticals, wherein the pharmaceuticals include antimicrobials, antivirals, antifungals, and neuroprotectives.

According to various embodiments of the invention, the particle may be a nano-particle having a size of 20-100 nm. According to various other embodiments, the particle may be a micro-particle having a size of 100-200 nm. According to still further embodiments, the composition may include both nano- and micro-particles complexed to a photosynthetic organism.

According to various further embodiments of the invention, the nano- and/or micro-particles of the invention may have any shape, including spheres, rods, fibers, films, wires, and tubes.

According to further embodiments of the invention, the relative concentration of nano- and/or micro-particles to microorganism cells may be 1:4, 1:2, 1:1, 2:1, or 4:1.

According to a most preferred embodiment, the composition may include a gold nano-particle of 200 nm complexed to $F.$ $diplosiphon$ cells in a ratio of 1:1.

According to further embodiments, various surface modifications can provide a stronger attachment of the nano-particle to the cell surface, further enhancing light capture and scatter, and hence photosynthetic pigment accumulation, lipid and other bio-product production.

According to further embodiments of the invention, the nano-particle-photosynthetic microorganism complexes of the invention may be grown in bioreactors having an artificial light source with specific and predetermined light wavelengths and/or light pulsations tuned to the absorbance profile of the complexes to increase microorganism growth and production of desired bioproducts.

According to other embodiments of the invention, the nano-particle-photosynthetic microorgansim complexes of the invention may be used in batch, batch-fed, recycling, fluidized bed and/or hollow-fiber bioreactors to increase the efficacy of photosynthesis for the production of the resulting bioproducts.

According to other embodiments of the invention, a composition is provided including a photosynthetic microorganism and a solution of zero-valent iron nanoparticles. According to a further embodiment of the invention, a method is provided for increasing photosynthetic organism biomass including growing cultures of the photosynthetic microorganism, and exposing the cultures to zero-valent iron nanoparticles. According to a further embodiment of the invention, a method is provided for increasing lipid production of a photosynthetic organism including growing cultures of the photosynthetic microorganism and exposing the cultures of said photosynthetic microorganism to zero-valent iron nanoparticles. The photosynthetic microorganism may a cyanobacteria, including $F.$ $diplosiphon$, optionally selected from $F.$ $diplosiphon$ strains B481 and SF33. $F.$ $diplosiphon$ strain B481 has been deposited at the UTEX Culture Collection of Algae, 205 W. $24^{th}$ St. Biological Labs 218, The University of Texas at Austin. Austin. TX 78712 under accession number 481 (https://utex.org.products/utex-b-0481?variant=30991885467738 [utex.org]).

According to further embodiments of the invention, the zero-valent iron nanoparticles may have an average size of 50 nm and an average surface area of 20-25 $m^2/g$, and may have a biodegradable organic coating of tetraethyl orthosilicate. According to a further embodiment of the invention, the zero-valent iron nanoparticles may be Nanofer 25s.

According to a further embodiment of the invention, the zero-valent iron nanoparticles are present in a concentration of between about 0.2 to about 1.6 mg/L of the photosynthetic microorganism.

DETAILED DESCRIPTION

Figure 1:
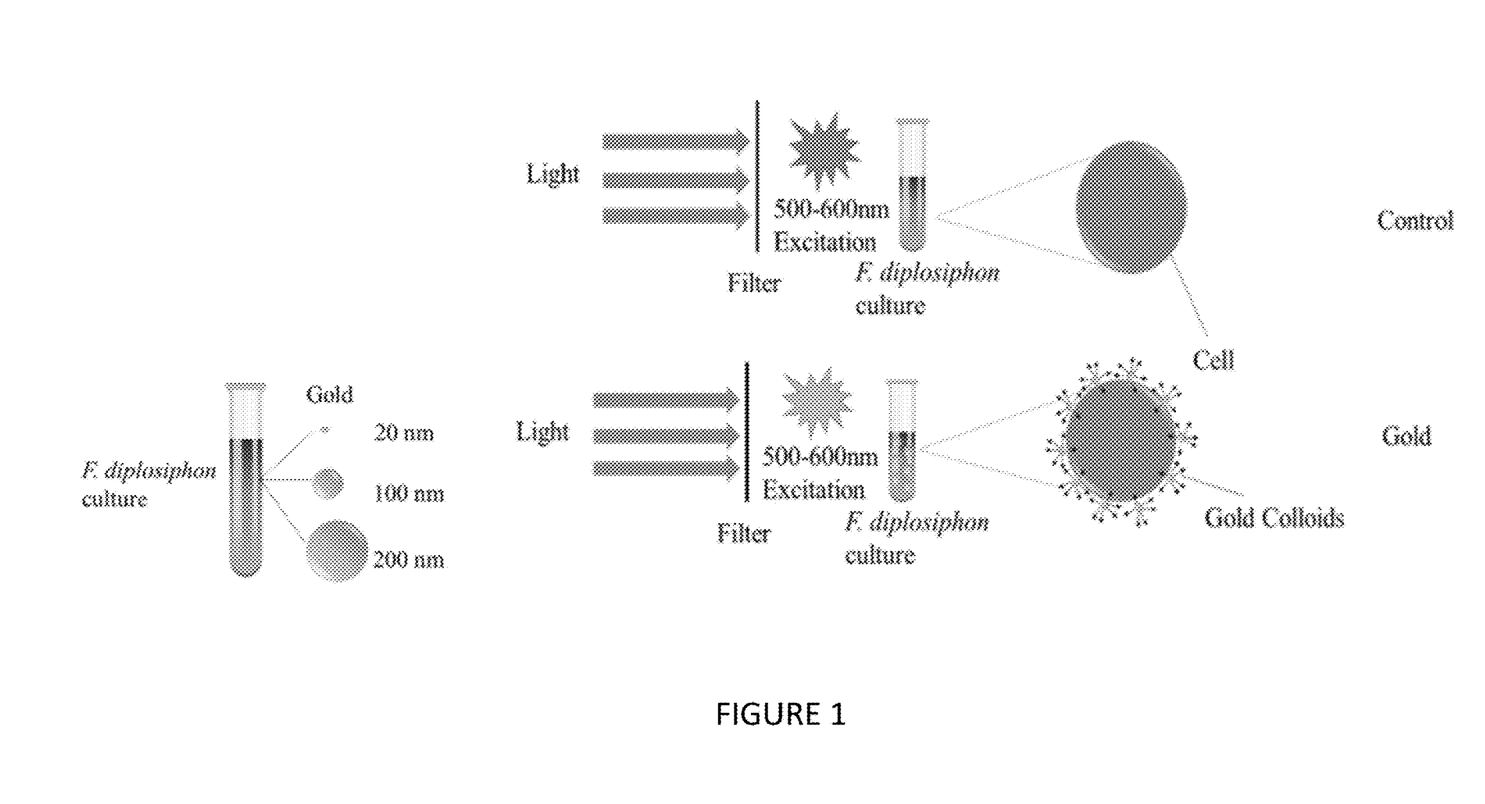
FIG. 1 is a representation of selected experiments that were used to demonstrate aspects of the invention.
Figure 2:
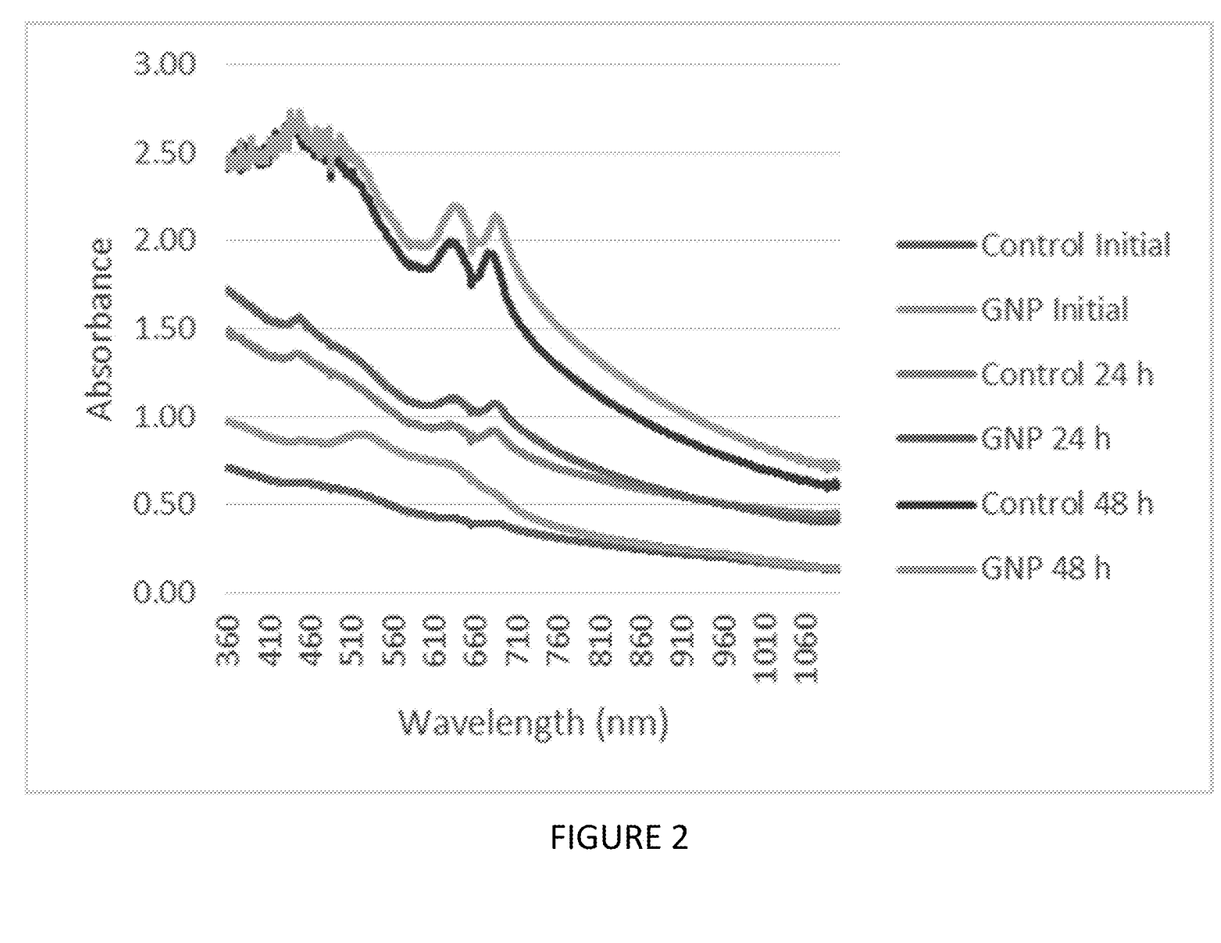
FIG. 2 is a line graph showing absorbance versus wavelength for $F.$ $diplosiphon$ cells loaded with gold nano-particles ("GNP").

The inventors have developed artificial light harvesting complexes in *F. diplosiphon* using gold nano-particles, taking advantage of the discovery that the wavelengths of light at which gold nano-particles are excited correspond to the wavelengths of light that are utilized by *F. diplosiphon* for photosynthesis. FIG. 1 shows a graphic depiction of experiments conducted by the inventors in connection with the making of this invention, using gold nano-particles with *F. diplosiphon* cells. Gold nano-particles are non-toxic to the growth of *F. diplosiphon*, and FIG. 2 shows that the nano-cultures (gold nano-particles in solution with *F. diplosiphon* cells) have a faster growth rate than *F. diplosiphon* non-complexed cell cultures. More specifically, FIG. 2 shows that a 1:1 ratio of 20 nm gold nano-particles to *F. diplosiphon* cells produces enhanced spectral absorbance at wavelengths corresponding to chlorophyll a and phycobiliproteins as well as at 750 nm (orange and blue lines), indicating an increase in photosynthetic pigment accumulation after 48 hrs.

Figure 3:
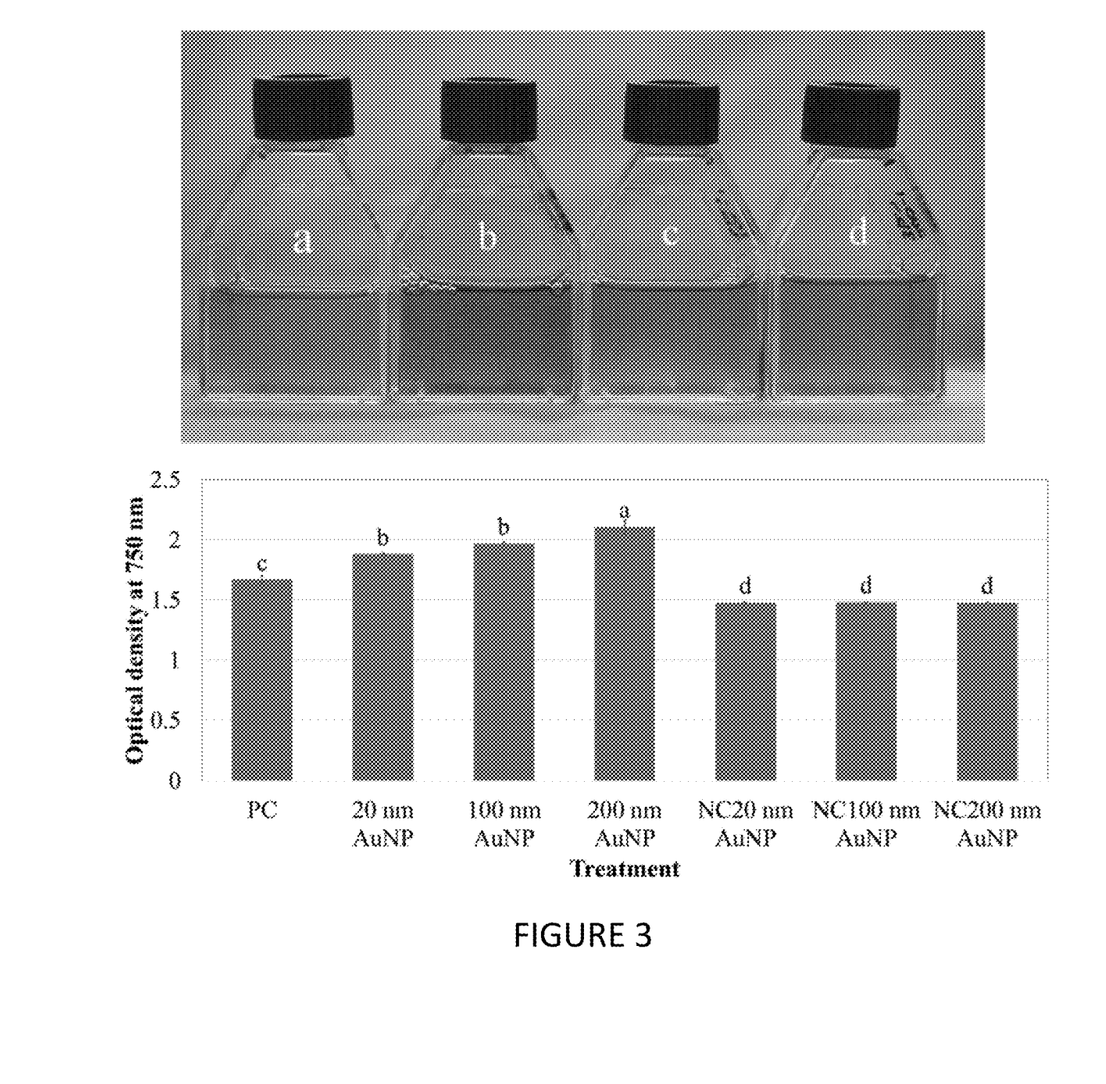
FIG. 3 shows culture flasks containing $F.$ $diplosiphon$ cells loaded with different size gold-nano-particles ("AuNP") (top) and a bar graph showing optical densities at 750 nm for those cultures (bottom).

Additionally, cultures of *F. diplosiphon* exposed to gold nano-particles exhibited higher optical densities at 750 nm ($OD_{750}$), which is commonly used to measure culture growth since changes in pigmentation will not interfere with absorbance at this wavelength. Referring to FIG. 3, *F. diplosiphon* was cultivated in culture flasks without nano-particles (flask a), and in solution with 20 nm (flask b), 100 nm (flask c), and 200 nm (flask d) gold colloids, see top of FIG. 3. After nine days, a significant increase in *F. diplosiphon* growth (measured by $OD_{750}$) was observed in cultures treated with 20, 100, and 200 nm gold nano-particles with maximum increase in growth observed in cultures treated with 200 nm gold nano-particles ("AuNPs"), see data bottom of FIG. 3. Cells grown in the absence of gold nano-particles served as positive control (PC) and gold colloids alone served as negative controls (NC).

Figure 4:
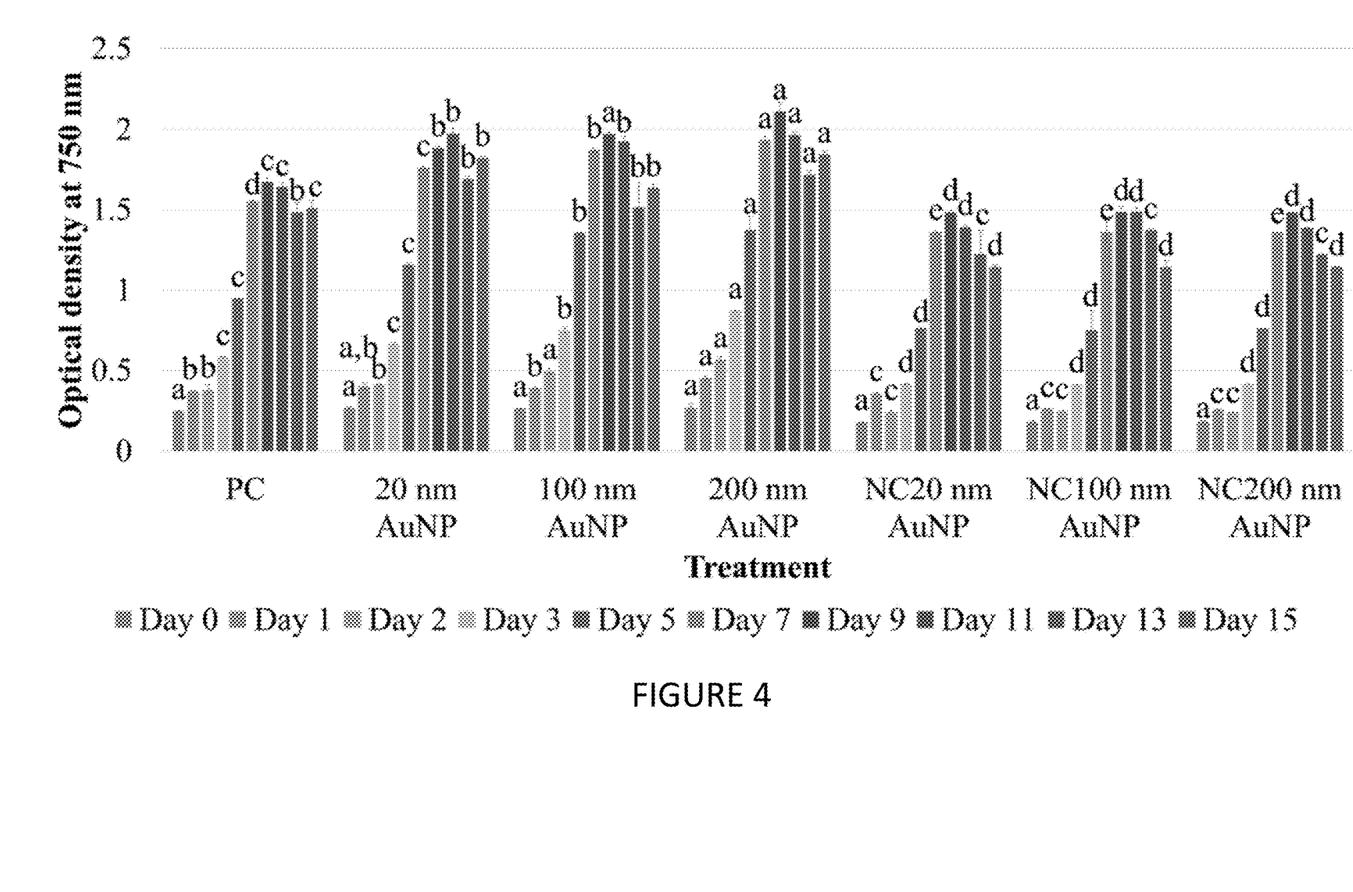
FIG. 4 is a bar graph showing optical densities at 750 nm for cultures of $F.$ $diplosiphon$ cells loaded with different size gold nano-particles ("AuNP") over time.

In addition, impact of 20, 100, and 200 nm-diameter AuNPs on *F. diplosiphon* growth was determined by measuring $OD_{750}$ over a period of 15 days. Cells grown in the absence of AuNPs served as positive control (PC) and AuNP suspensions served as negative controls (NC). While all other treatments achieved peak growth by the ninth day, cultures in solution with 20 nm AuNPs exhibited prolonged growth to 11 days (FIG. 4).

Figure 5:
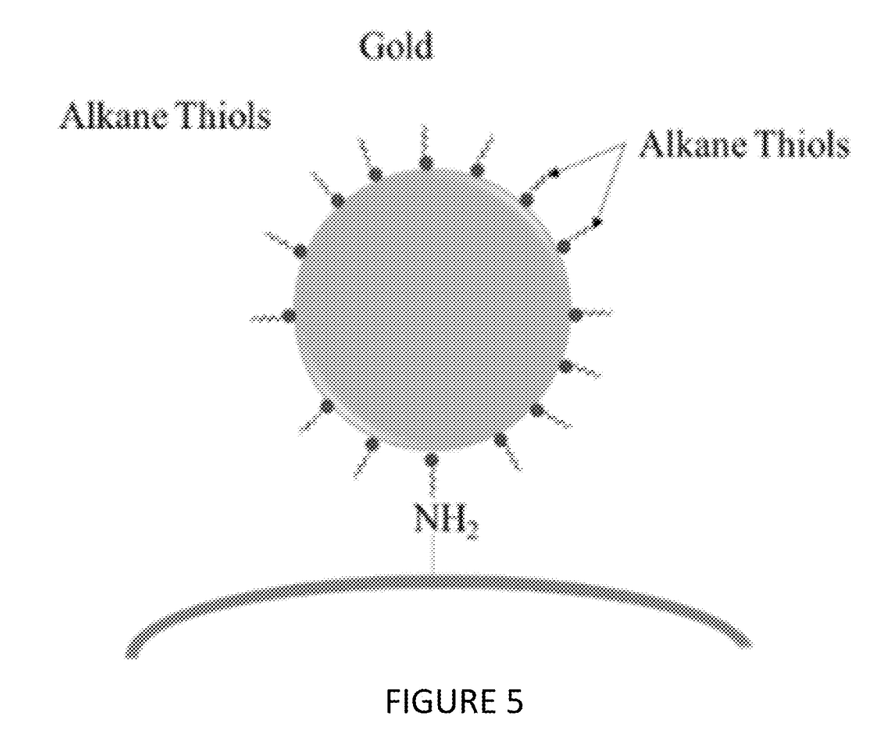
FIG. 5 is a representation of a surface-modified gold nano-particle complexed to a photosynthetic microorganism.

FIG. 5 shows self-assembled monolayers of alkane thiols binding to the surface of the AuNPs to enhance photosynthesis of a complexed microorganism. Such surface modifications can provide a stronger attachment of the nanoparticle to the cell surface, further enhancing light capture and scatter, and hence photosynthetic pigment accumulation, lipid and other bio-product production.

The inventors have also discovered that *F. diplosiphon* cultures exposed to coated zero-valent iron nanoparticles show increased growth and lipid content. Cultures of two different strains of *F. diplosiphon* were exposed to two different zero-valent iron nanoparticles ("nZVIs"), Nanofer 25 and Nanofer 25 s, ranging from 0.05-3.2 mg $L^{-1}$ the organism. Both Nanofers had an average size of 50 nm, surface area of 20-25 $m^2$/g, and a high content of iron. Nanofer 25 s contained a biodegradable organic coating of tetraethyl orthosilicate. *F. diplosiphon* strains (B481 and SF33) were grown in BG11/HEPES containing 0.05, 0.1, 0.2, 0.4, 0.8, 1.6, and 3.2 mg $L^{-1}$ of each nanoparticle. Cultures containing Fe-EDTA (0.5 mg $L^{-1}$ Fe) served as control. Three replicates were maintained and cultures were grown for 15 days under constant shaking at 28° C. and 70 rpm, with an initial optical density of 0.1 at 750 nm. In addition, chlorophyll a (chlα), carotenoids, and phycobiliproteins quantified to test the impact of nZVIs on photosynthetic efficiency.

Figure 6:
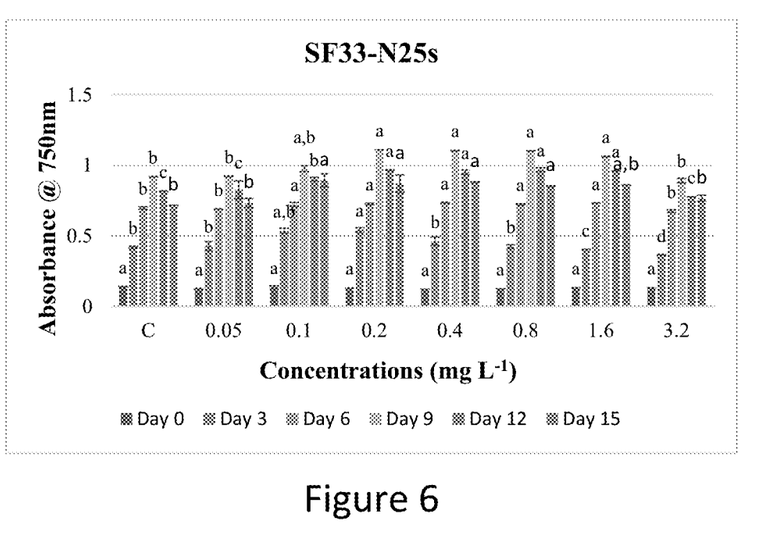
FIG. 6 shows growth of $F.$ $diplosiphon$ SF33 strain in BG11/HEPES medium with 0.05, 0.1, 0.2, 0.4, 0.8, 1.6 and 3.2 $mgL^{-1}$ Nanofer 25s and untreated control over a period 15 days. Average optical density at 750 nm (±standard error) for three biological replicates is shown for each time point. Different letters above the final time point indicate significance among treatment means ($P>0.05$).
Figure 7:
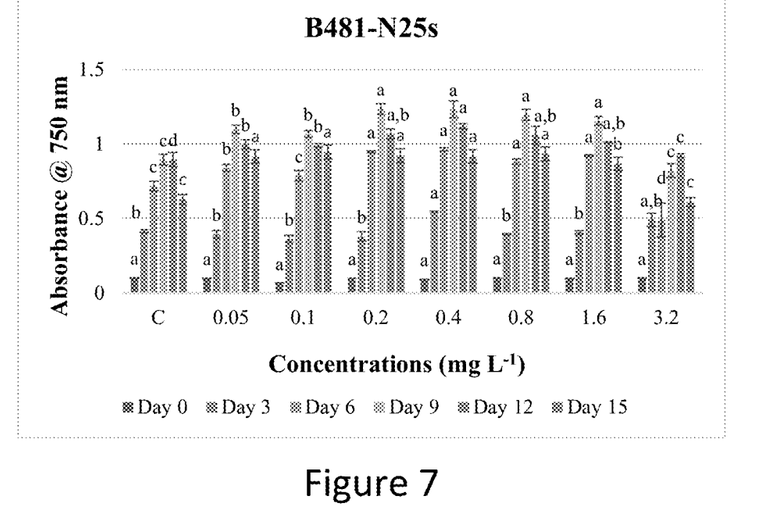
FIG. 7 shows growth of $F.$ $diplosiphon$ B481 strain in BG11/HEPES medium with 0.05, 0.1, 0.2, 0.4, 0.8, 1.6 and 3.2 $mgL^{-1}$ Nanofer 25s and untreated control over a period 15 days. Average optical density at 750 nm (±standard error) for three biological replicates is shown for each time point. Different letters above the final time point indicate significance among treatment means ($P>0.05$).

Significant increases (P<0.05) in growth were observed in B481 (28%, 27%, 25%, and 23%) and SF33 (17.5%, 17%, 20%, and 14%) strains exposed to 0.2, 0.4, 0.8 and 1.6 mg $L^{-1}$ Nanofer 25s respectively (FIGS. 6 and 7), relative to controls. Nano-treated cultures exposed to 0.05, 0.1, and 3.2 mg $L^{-1}$ Nanofer 25s did not exhibit significant differences (P<0.05) in growth (FIGS. 6 and 7). In addition, *F. diplosiphon* exposed to Nanofer 25 at concentrations ranging from 0.05-3.2 mg $L^{-1}$ did not exhibit significant differences (P>0.05) in growth compared to control. No significant differences (P>0.05) in chlα, carotenoid, and phycobiliprotein levels were observed in *F. diplosiphon* exposed to Nanofer 25s ranging from 0.4-1.6 mg $L^{-1}$ relative to control.

Since both *F. diplosiphon* strains B481 and SF33 exposed to Nanofer 25s ranging from 0.2-1.6 mg $L^{-1}$ revealed a significant improvement in growth, cultures grown in this range of concentrations of Nanofer 25s were examined to determine lipid content.

Total lipid content in the cultures of *F. diplosiphon* B481 and SF33 cultures treated with 0.2, 0.4, 0.8 and 1.6 mg $L^{-1}$ Nanofer 25s was determined using the chloroform:methanol extraction method based on Folch, et al. [1957], followed by conversion to FAMEs via direct transesterification.

Figure 8:
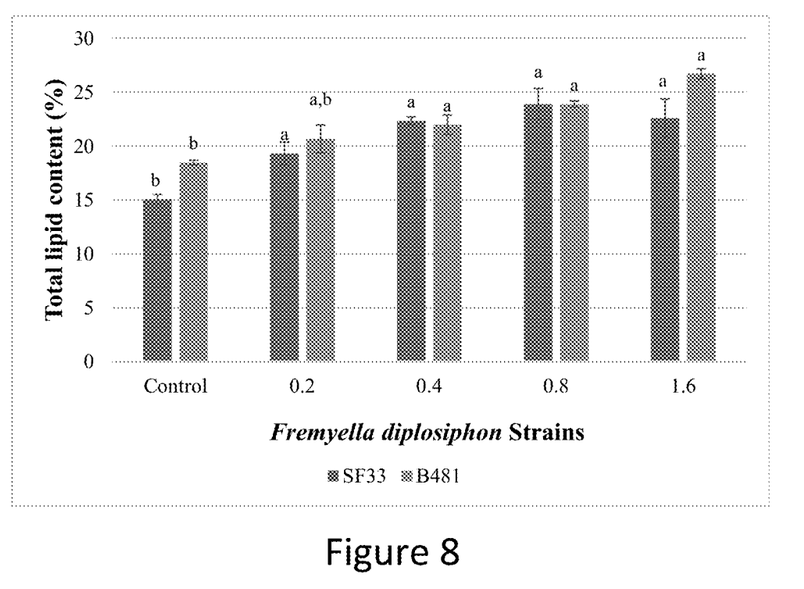
FIG. 8 shows a comparison of total lipid content in $F.$ $diplosiphon$ SF33 and B481 strains (control) and cultures amended with 0.2, 0.4, 0.8 and 1.6 mg $L^{-1}$ Nanofer 25 s. Average percent lipid content (±standard error) of three biological replicates for each strain is shown. Different letters above bars indicate significance among treatment means ($P>0.05$).

Gravimetric analysis revealed significant increases (P<0.05) in total lipid content of strain B481 (19.02%, 29.29%, and 44.51%) when exposed to 0.4, 0.8 and 1.6 mg $L^{-1}$ Nanofer 25 s. In addition, significant increases (P<0.05) in SF33 total lipid yield (28.13%, 48.2%, 58.45%, and 49.75%) were observed in cultures grown in 0.2 to 1.6 mg $L^{-1}$ Nanofer 25s (FIG. 8).

FAME compositions of *F. diplosiphon* transesterified lipids were determined using a Shimadzu GC17A/QP5050A GC-MS combination. The GC17A was equipped with a low-polarity (5% phenyl-, 95% methyl-siloxane) capillary column (30 m length, 0.25 mm ID, 0.25 μm film thickness, and 10 m length guard column). Peaks were identified by comparing mass spectra to The Lipid Web Archive of FAME Mass Spectra. To identify additional FAMEs from the *F. diplosiphon* nano-treated cells and control, high-resolution two-dimensional gas chromatography with time-of-flight mass spectrometry (GC×GC-TOFMS) was used. Total lipids were extracted and subjected to direct transesterification. For all experiments, three biological replicates were maintained and the experiment was repeated once. The chemical and physical properties of the transesterified lipids from FAME composition (w %) in control and nano-treated cells were calculated using Biodiesel Analyzer software Version 2.2.

Saturated and unsaturated FAMEs were detected in *F. diplosiphon* nano-treated cultures and the untreated control as shown in Tables 1 and 2.

TABLE 1

Breakdown of saturated and unsaturated fatty acid methyl ester (FAME) proportions in *F. diplosiphon* SF33 control and cultures treated with 0.2, 0.4, 0.8 and 1.6 mg L$^{-1}$ Nanofer 25s.

| | FAME Type (%) | | Ratio of FAME Saturated/ |
|---|---|---|---|
| Strains | Saturated | Unsaturated | Unsaturated |
| SF33 control | 88.64 | 11.44 | 7.75 |
| SF33 + 0.2 mg L$^{-1}$ N25s | 65.78 | 34.22 | 1.92 |
| SF33 + 0.4 mg L$^{-1}$ N25s | 62.67 | 37.33 | 1.68 |
| SF33 + 0.8 mg L$^{-1}$ N25s | 71.66 | 28.34 | 2.53 |
| SF33 + 1.6 mg L$^{-1}$ N25s | 50.50 | 49.50 | 1.02 |

TABLE 2

Breakdown of saturated and unsaturated fatty acid methyl ester (FAME) proportions in *F. diplosiphon* B481 control and cultures treated with 0.2, 0.4, 0.8 and 1.6 mg L$^{-1}$ Nanofer 25s.

| | FAME Type (%) | | Ratio of FAME Saturated/ |
|---|---|---|---|
| Strains | Saturated | Unsaturated | Unsaturated |
| B481 control | 77.27 | 22.74 | 3.40 |
| B481 + 0.2 mg L$^{-1}$ N25s | 69.11 | 30.95 | 2.23 |
| B481 + 0.4 mg L$^{-1}$ N25s | 62.00 | 36.97 | 1.68 |
| B481 + 0.8 mg L$^{-1}$ N25s | 58.35 | 41.72 | 1.40 |
| B481 + 1.6 mg L$^{-1}$ N25s | 63.51 | 36.50 | 1.74 |

Figure 9:
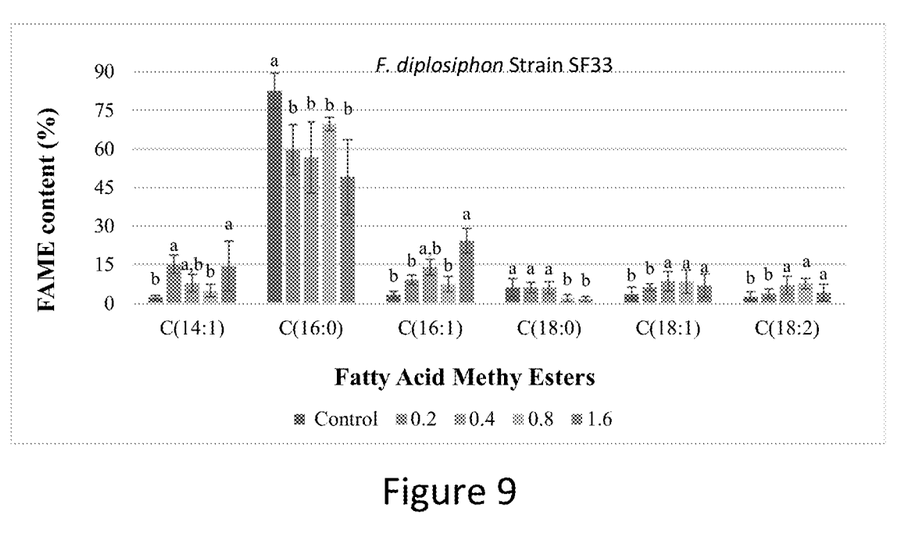
FIG. 9 shows a comparison of fatty acid methyl ester (FAME) composition of $F.$ $diplosiphon$ SF33 strain total lipids subjected to direct transesterification in the absence of iron nanoparticle and in solution amended with 0.2, 0.4, 0.8 and 1.6 mg $L^{-1}$ Nanofer 25 s. Average percent FAME content (±standard error) for three biological replicates of each strain is shown. Different letters above bars indicate significance among treatment means ($P>0.05$).
Figure 10:
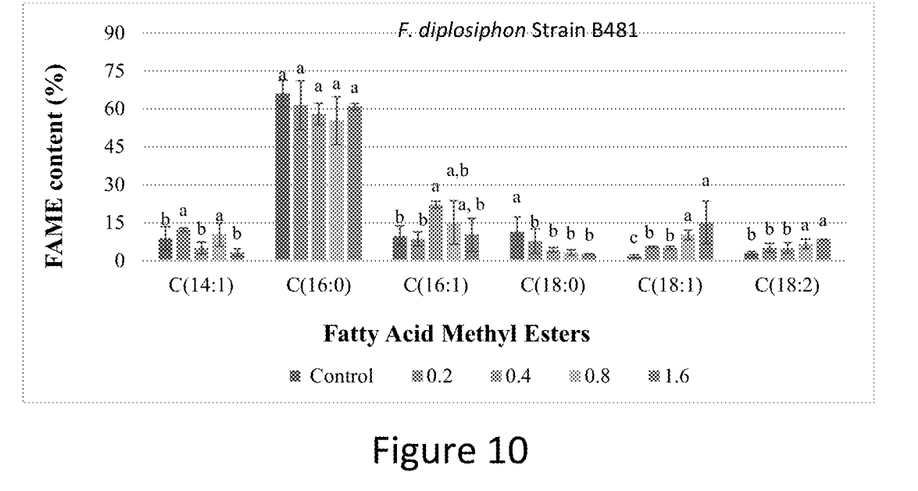
FIG. 10 shows a comparison of fatty acid methyl ester (FAME) composition of $F.$ $diplosiphon$ B481 strain total lipids subjected to direct transesterification in the absence of iron nanoparticle and in solution amended with 0.2, 0.4, 0.8 and 1.6 $mgL^{-1}$ Nanofer 25 s. Average percent FAME content (±standard error) for three biological replicates of each strain is shown. Different letters above bars indicate significance among treatment means ($P>0.05$).
Figure 11:
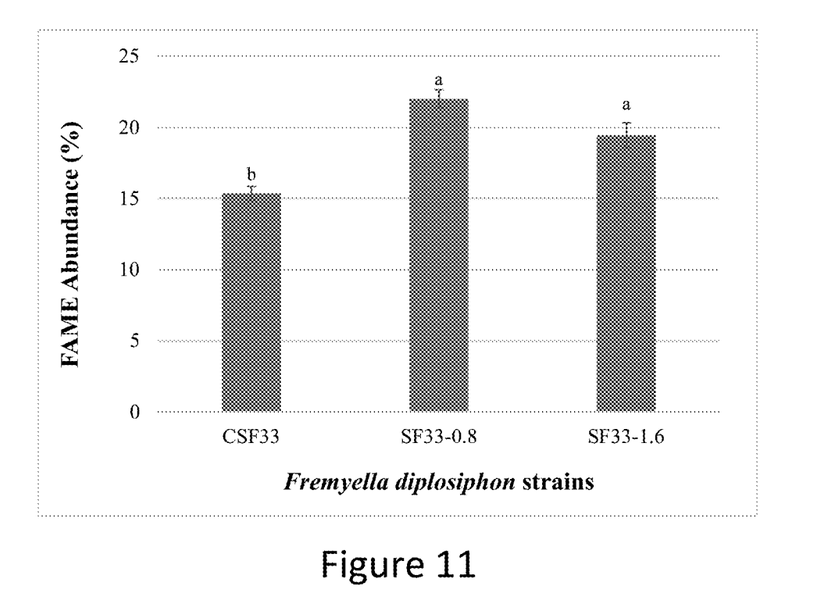
FIG. 11 shows fatty acid methyl ester (FAME) abundance in transesterified extractable lipids of $F.$ $diplosiphon$ SF33 control and nanotreated cells (0.8 and 1.6 mg/L) determined using GC×GC-TOFMS. Average percent FAME content (±coefficient of variation) of each strain for three biological replicates is shown. Different letters above bars indicate significance among treatment means (P<0.05).

Methyl palmitate which is the methyl ester of hexadecanoic acid (C16:0) was detected as the dominant FAME in all *F. diplosiphon* nano-treated and control cultures (FIGS. 9 and 10). This component accounted for 82.55%, 59.67%, 56.64%, 69.69%, and 49.05% of total FAMEs produced from SF33 treated with Nanofer 25s ranging from 0-1.6 mg L$^{-1}$ total lipids (Table 3) and 66.00%, 61.43%, 57.87%, 55.42%, and 60.95% from B481 treated with the same concentrations (Table 4).

Additional FAME components such as methyl tetradecanoate (C14:1), methyl hexadecanoate (C16:1), methyl octadecanoate (C18:0), methyl octadecenoate (C18:1), and methyl octadecadienoate (C18:2) were detected in all *F. diplosiphon* cultures (FIGS. 9 and 10; Tables 3 and 4). While a significant increase (P<0.05) in methyl octadecenoate (C18:1) and methyl octadecadienoate (C18:2) levels was observed from SF33 transesterified lipids exposed to 0.4, 0.8 and 1.6 mg L$^{-1}$ Nanofer 25s, no significant differences (P>0.05) exhibited in cultures treated with 0.2 mg L$^{-1}$ transesterified lipids (FIGS. 8 and 9). In addition, a significant increase (P<0.05) in methyl octadecenoate (C18:1) and methyl octadecadienoate (C18:2) levels from B481 treated with 0.8 and 1.6 mg L$^{-1}$ Nanofer 25s transesterified lipids was observed. However, SF33 and B481 transesterified lipids treated with 0.2 and 0.4 mg L$^{-1}$ Nanofer 25s, did not reveal significant differences (P>0.05) (FIGS. 9 and 10).

TABLE 3

Fatty acid methyl ester (FAME) composition in *F. diplosiphon* SF33 control and cultures treated with 0.2, 0.4, 0.8 and 1.6 mg L$^{-1}$ Nanofer 25s.

| FAME | Control | 0.2 mg L$^{-1}$ | 0.4 mg L$^{-1}$ | 0.8 mg L$^{-1}$ | 1.6 mg L$^{-1}$ |
|---|---|---|---|---|---|
| Methyl myristate (C14:1) | 2.19 | 15.07 | 7.82 | 4.98 | 14.36 |
| Methyl palmitate (C16:0) | 82.55 | 59.67 | 56.64 | 69.69 | 49.05 |
| Methyl hexadecanoate (C16:1) | 3.33 | 9.16 | 14.02 | 7.39 | 24.27 |
| Methyl octadecanoate (C18:0) | 6.09 | 6.11 | 6.03 | 1.97 | 1.45 |
| Methyl octadecenoate (C18:1) | 3.44 | 6.19 | 8.48 | 8.35 | 6.81 |
| Methyl octadecadienoate (C18:2) | 2.49 | 3.80 | 7.01 | 7.63 | 4.06 |

TABLE 4

Fatty acid methyl ester (FAME) composition in *F. diplosiphon* B481 control and cultures treated with 0.2, 0.4, 0.8 and 1.6 mg L$^{-1}$ Nanofer 25s.

| FAME | Control | 0.2 mg L$^{-1}$ | 0.4 mg L$^{-1}$ | 0.8 mg L$^{-1}$ | 1.6 mg L$^{-1}$ |
|---|---|---|---|---|---|
| Methyl myristate (C14:1) | 8.73 | 12.20 | 4.92 | 10.17 | 3.10 |
| Methyl palmitate (C16:0) | 66.00 | 61.43 | 57.87 | 55.24 | 60.95 |
| Methyl hexadecanoate (C16:1) | 9.66 | 8.45 | 22.01 | 15.00 | 10.09 |
| Methyl octadecanoate (C18:0) | 11.27 | 7.68 | 4.13 | 3.10 | 2.56 |
| Methyl octadecenoate (C18:1) | 1.49 | 5.32 | 5.04 | 10.09 | 15.02 |
| Methyl octadecadienoate (C18:2) | 2.86 | 4.98 | 5.01 | 6.46 | 8.29 |

Figure 12:
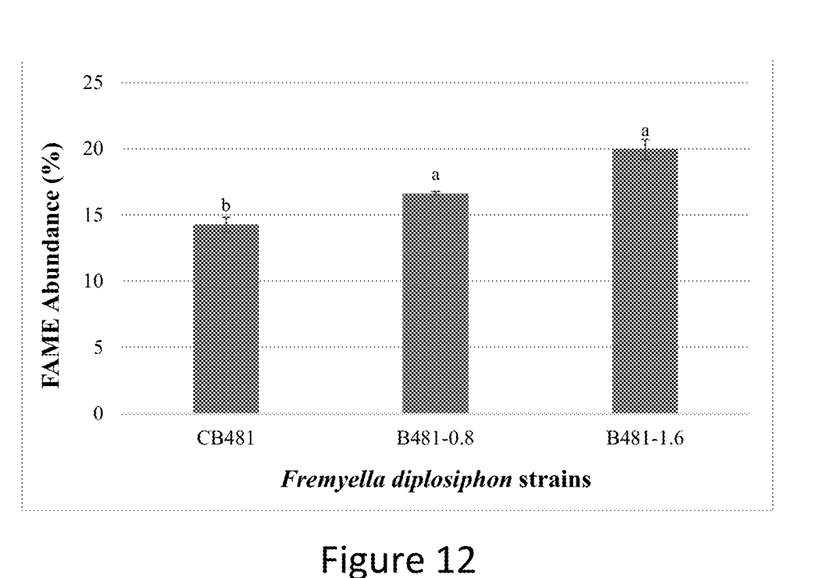
FIG. 12 shows fatty acid methyl ester (FAME) abundance in transesterified extractable lipids of *F. diplosiphon* B481 control and nano-treated cells (0.8 and 1.6 mg/L) determined using GC×GC-TOFMS. Average percent FAME content (±coefficient of variation) of each strain for three biological replicates is shown. Different letters above bars indicate significance among treatment means (P<0.05).

In addition to conventional GC-MS, high-resolution GC×GC-TOFMS was used to further separate polar and aromatic compounds. GC×GC-TOFMS analysis revealed the presence of FAMEs with numbers of carbon (C) from 12-18, double bonds from 0-4, and alkanes from C11 to C34. FAME abundance in SF33 and B481 strains treated with 0.8 and 1.6 mg L$^{-1}$ Nanofer 25s was significantly higher (P<0.05) than the control (FIGS. 12 and 13). FAME components such as C18:3 and C18:4 not detected in conventional GC-MS were identified by GC×GC-TOFMS. Significantly higher (P<0.05) methyl octadecatrienoate (C18:3) was found in SF33 strain supplemented with 0.8 and 1.6 mg L$^{-1}$ Nanofer 25s (16% and 13.41% transesterified lipids). In addition, octadecatrienoic acid (C18:3) in B481 strain treated with 0.8 and 1.6 mg L$^{-1}$ Nanofer 25s (49.13% and 14.67% transesterified lipids) was also significantly higher (P<0.05) compared to the control. Methyl stearidonate (C18:4) in SF33 strain treated with 0.8 and 1.6 mg L$^{-1}$ Nanofer 25s (20.83% and 16% transesterified lipids) was significantly lower (P<0.05). However, B481 strain treated with 0.8 and 1.6 mg L$^{-1}$ Nanofer 25s exhibited significant increases (P<0.05) in methyl stearidonate (C18:4) (62.73% and 31.95% transesterified lipids) compared to the control.

Calculation of chemical and physical biofuel properties revealed products with a high cetane number (62.6-68.81 for SF33 and 63.0-67.74 for B481) and oxidative stability (49.38-18.04 h for SF33 and 43.82-16.81 h for B481). In addition, various values relevant to biodiesel performance were observed, including density (0.868-0.870 g/cm$^3$ for SF33 and 0.861-0.870 g/cm$^3$ for B481), viscosity (3.508-3.808 mm$^2$/s for SF33 and 3.588-3.759 mm$^2$/s for B481), and iodine (11.56-37.70 g $I_2$/100 g for SF33 and 16.16-38.59 g $I_2$/100 g for B481) in all *F. diplosiphon* cultures (Table 5 and 6).

TABLE 5

Biodiesel properties of *F. diplosiphon* SF33 in the absence of iron nanoparticle and cultures with 0.2, 0.4, 0.8 and 1.6 mg $L^{-1}$ Nanofer 25s transesterified lipids.

| Biodiesel Properties | Control | 0.2 mgL$^{-1}$ | 0.4 mgL$^{-1}$ | 0.8 mgL$^{-1}$ | 1.6 mgL$^{-1}$ |
|---|---|---|---|---|---|
| Saponification Value (mg KOH/g fat) | 217.314 | 219.319 | 216.413 | 216.344 | 220.219 |
| Iodine Value (g $I_2$/100 g) | 11.564 | 21.595 | 34.321 | 28.708 | 37.709 |
| Cetane number | 68.814 | 66.327 | 63.798 | 65.069 | 62.6 |
| Long Chain Saturated Factor | 10.181 | 9.022 | 8.679 | 7.954 | 5.63 |
| Cold Filter Plugging Point (° C.) | 15.509 | 11.867 | 10.79 | 8.512 | 1.211 |
| Cloud Point (° C.) | 39.434 | 26.394 | 24.801 | 31.665 | 20.808 |
| Pour Point (° C.) | 35.987 | 21.832 | 20.101 | 27.553 | 15.768 |
| Allylic Position Equivalent | 8.66 | 13.79 | 22.5 | 23.61 | 14.93 |
| Bis-Allylic Position Equivalent | 2.52 | 3.8 | 7.01 | 7.63 | 4.06 |
| Oxidation Stability (h) | 49.388 | 33.625 | 19.414 | 18.047 | 31.637 |
| Higher Heating Value (mJ/kg) | 39.244 | 39.116 | 39.18 | 39.199 | 39.053 |
| Kinematic Viscosity (mm$^2$/s) | 3.808 | 3.651 | 3.681 | 3.718 | 3.508 |
| Density (g/cm$^3$) | 0.868 | 0.868 | 0.87 | 0.869 | 0.87 |

TABLE 6

Biodiesel properties of *F. diplosiphon* B481 in the absence of iron nanoparticle and cultures with 0.2, 0.4, 0.8 and 1.6 mgL$^{-1}$ Nanofer 25s transesterified lipids.

| Biodiesel Properties | Control | 0.2 mgL$^{-1}$ | 0.4 mgL$^{-1}$ | 0.8 mgL$^{-1}$ | 1.6 mgL$^{-1}$ |
|---|---|---|---|---|---|
| Saponification Value (mg KOH/g fat) | 217.659 | 218.284 | 215.022 | 217.602 | 214.292 |
| Iodine Value (g $I_2$/100 g) | 16.165 | 22.241 | 35.582 | 35.751 | 38.597 |
| Cetane number | 67.739 | 66.3 | 63.678 | 63.339 | 63.086 |
| Long Chain Saturated Factor | 12.235 | 9.983 | 7.852 | 7.074 | 7.375 |
| Cold Filter Plugging Point (° C.) | 21.962 | 14.887 | 8.192 | 5.747 | 6.693 |
| Cloud Point (° C.) | 29.724 | 27.32 | 25.448 | 24.064 | 27.068 |
| Pour Point (° C.) | 25.446 | 22.837 | 20.804 | 19.302 | 22.562 |
| Allylic Position Equivalent | 7.21 | 15.28 | 15.06 | 23.01 | 31.6 |
| Bis-Allylic Position Equivalent | 2.86 | 4.98 | 5.01 | 6.46 | 8.29 |
| Oxidation Stability (h) | 43.825 | 26.271 | 26.129 | 20.846 | 16.816 |
| Higher Heating Value (mJ/kg) | 39.186 | 39.175 | 38.753 | 39.167 | 39.242 |
| Kinematic Viscosity (mm$^2$/s) | 3.759 | 3.696 | 3.588 | 3.631 | 3.737 |
| Density (g/cm$^3$) | 0.867 | 0.869 | 0.861 | 0.87 | 0.87 |

While the application of nZVIs in green technologies can be toxic to microorganisms due to damage caused by ROS activity (Sevcu et al. 2011), these studies show that specific concentrations in *F. diplosiphon* resulted in enhanced lipid production. An increase of 28% to 58% in total lipid content in SF33 exposed to Nanofer 25s ranging from 0.2 to 1.6 mg $L^{-1}$, and 19% to 44% in B481 treated with 0.4, 0.8, and 1.6 mg $L^{-1}$ (FIG. 8). This indicates that Nanofer 25s is an ideal nZVI to augment FAMEs in *F. diplosiphon*.

Quantification of total lipid content provides valuable information about the organism's lipid capacity; however, it is not determinative for biofuel potential since this includes not only FAs but also all cellular lipids. Thus, it is essential to evaluate the FAME composition of *F. diplosiphon* transesterified lipids and calculate their physical and chemical properties to gain a more comprehensive understanding of its resultant biofuel quality and production capacity. Increased methyl octadecadienoate (C18:1) and methyl octadecadienoate (C18:2) abundance in *F. diplosiphon* SF33 and B481 nano-treated cells (FIGS. 9 and 10) shows that iron nanoparticles enhanced unsaturated FAMEs which are primary components of biofuel. In addition, increased total lipid content and essential unsaturated FAs for biodiesel production, such as oleic and linoleic acids in nano-treated cultures indicates that Nanofer 25s is a suitable nZVI to enhance *F. diplosiphon* biofuel potential.

Significant increase in FAME abundance of *F. diplosiphon* exposed to 0.8 and 1.6 mg $L^{-1}$ Nanofer 25s (FIGS. 12 and 13) as well as the identification of FAME components such as C18:3 and C18:4 which were not detected in 1D GC-MS suggesting that *F. diplosiphon* nano-treated cultures will have higher biodiesel capacity due to the increase in proportion of unsaturated FAMEs.

In summary, the present invention is the use of Nanofer 25s nZVI to increase microorganism/cyanobacterial growth, total lipid content, as well as oleic and linoleic acids, which are primary fatty acid components in biofuel production. Enhancing *F. diplosiphon* lipid productivity will enhance harvest efficiency of the resultant biofuel. In addition, enhancement of unsaturated FA profile benefits *F. diplosiphon*-derived biodiesel by reducing the cloud and pour points, thus increasing the percentage that could be used in commercial blends.

The invention claimed is:

1. A composition comprising cyanobacteria *F. diplosiphon* and a solution of zero-valent iron nanoparticles having a biodegradable coating of tetraethyl orthosilicate, and wherein said composition has enhanced lipid production as compared to cyanobacteria *F. diplosiphon* cultured in the absence of zero-valent iron nanoparticles.

2. A composition according to claim 1, wherein said *F. diplosiphon* is strain B481.

3. A composition according to claim 1, wherein said zero-valent iron nanoparticles have an average size of 50 nm and an average surface area of 20-25 m$^2$/g.

4. A composition according to claim 1, wherein said zero-valent iron nanoparticles are Nanofer 25s.

5. A composition according to claim 1, wherein said zero-valent iron nanoparticles are present in a concentration of between about 0.2 to about 1.6 mg/L of photosynthetic microorganism.

* * * * *